United States Patent
Butler et al.

[11] Patent Number: 5,937,852
[45] Date of Patent: Aug. 17, 1999

[54] APPARATUS FOR INDUCTION OF INHALED PHARMACOLOGICAL AGENT BY A PEDIATRIC PATIENT

[75] Inventors: Bruce D. Butler; R. David Warters, both of Houston, Tex.

[73] Assignee: The Board of Regents of The University of Texas System, Austin, Tex.

[21] Appl. No.: 08/939,486

[22] Filed: Sep. 29, 1997

Related U.S. Application Data

[63] Continuation-in-part of application No. 08/841,937, Apr. 8, 1997, Pat. No. 5,865,172.

[51] Int. Cl.[6] .................................................. A61M 15/00
[52] U.S. Cl. ................ 128/203.12; 128/202.22
[58] Field of Search ......................... 128/203.12, 200.23, 128/203.28, 203.14, 205.13, 205.11, 204.23, 204.29, 200.16, 202.22, 205.23; 434/264; 600/538, 539, 533

[56] References Cited

U.S. PATENT DOCUMENTS

| | | |
|---|---|---|
| 4,809,692 | 3/1989 | Nowacki et al. . |
| 4,832,015 | 5/1989 | Nowacki et al. . |
| 4,873,970 | 10/1989 | Freidank et al. .................... 128/202.22 |
| 4,945,918 | 8/1990 | Abernathy ............................... 128/719 |
| 5,042,467 | 8/1991 | Foley . |
| 5,167,506 | 12/1992 | Kilis et al. . |
| 5,363,842 | 11/1994 | Mishelevich et al. . |
| 5,517,983 | 5/1996 | Deighan et al. . |
| 5,522,380 | 6/1996 | Dwork . |
| 5,613,489 | 3/1997 | Miller et al. ........................ 128/203.28 |

OTHER PUBLICATIONS

Advertisement for DHD Healthcare, Canasotoa New York, *Introducing the ACE Aerosol Cloud Enhancer with exclusive*, detachable mask, 1 page.
Advertisement for Clement Clark Incorporated, Columbus, Ohio, Press Release The Windmill Trainer Improves Asthma Care, and The Windmill Trainer Instructions, 2 pages.

*Primary Examiner*—John G. Weiss
*Assistant Examiner*—Charles W. Anderson
*Attorney, Agent, or Firm*—Rosenblatt & Redano

[57] ABSTRACT

This invention relates to an apparatus for inducing a pediatric patient to inhale a fluid pharmacological agent through a face mask. The apparatus comprises a fluid conduit through which fluid pharmacological agent may be inhaled, and a visual patient stimulator coupled to said conduit and accuatable by inspiratory or expiratory flow through said conduit. The visual stimulator of the present invention changes color in response to changing gas levels which occur during inspiration and expiration.

18 Claims, 2 Drawing Sheets

APPARATUS FOR INDUCTION OF INHALED PHARMACOLOGICAL AGENT BY A PEDIATRIC PATIENT

REFERENCE TO RELATED APPLICATIONS

This application is a continuation in part of application Ser. No. 08/841,937, filed on Apr. 8, 1997, now U.S. Pat. No. 5,865,172 which is incorporated herein by reference.

BACKGROUND OF THE INVENTION

1. Field of the Invention

This invention relates to an apparatus for inducing a pediatric patient to inhale a fluid pharmacological agent through a face mask. The apparatus comprises a fluid conduit through which fluid pharmacological agent may be inhaled, and a visual patient stimulator coupled to said conduit and accuatable by inspiratory or expiratory flow through said conduit. The visual stimulator of the present invention changes color in response to changing gas levels which occur during inspiration and expiration.

2. Description of the Prior Art

In the medical arts, it is customary to deliver pharmacological agents to a patient. For instance, it is common to induce anesthesia in patients prior to many surgical procedures. A common method of inducing anesthesia is through the inhalation of pharmacological fluids through a face mask. The delivery of pharmacological agents through a face mask to a pediatric patient, particulary to a preschool age child, is often difficult. This difficulty is a result of many factors, including but not limited to a child's short attention span, fear, and/or an inability to comprehend the importance of inhaling pharmacological fluids.

The lack of cooperation exhibited by many pediatric patients during the course of attempting to administer pharmacological agents in fluid form can result in increased anxiety on the part of the patient, the patient's parents or guardians, and the anesthetist. There is also a risk of bodily injury to an uncooperative or combative patient. Such increased anxiety and lack of cooperation result in an increase in the time required to induce anesthesia in an uncooperative pediatric patient.

Common prior art procedures for inducing a pediatric patient to inhale pharmacological fluids for anesthesia are to allow the patient to first play with a face mask prior to the induction of pharmacological gas, so that the child becomes familiar and comfortable with mask ventilation. The term "pediatric patient" as used herein refers to young children as well as to older patients who exhibit the emotional, developmental, intellectual, and/or behavioral characteristics of young children.

The process of administering a fluid pharmacological agent comprises both inhalation or inspiration and exhalation or expiration by the patient. It is desirable to motivate the pediatric patient to maximize his breathing rate and volume of inhaled or inspired gases. The present invention provides an apparatus for inducing a pediatric patient to inhale pharmacological agent by providing a visual stimulus to the pediatric patient which induces the patient to maximize his inhalation of a pharmacological agent. An advantage of the present invention is the potential for decreased dosage or necessity of preoperative sedation.

The visual stimulus provided by the present invention is simple and inexpensive, requiring no electrical or electronic parts. This is one major advantage of the present invention over the inhaler devices of the prior art which involve complex and expensive electronics. Such prior art devices are disclosed in U.S. Pat. No. 5,636,842 to Mishelvich et al. and U.S. Pat. No. 5,167,506 to Kilis et al. Certain of these prior art devices, such as that disclosed in U.S. Pat. No. 5,167,506, use display screens which display text messages. Such text message screens are of little or no value with pediatric patients who have not yet learned to read.

Another advantage of the present invention is that the visual stimulus is easily visible to a pediatric patient breathing gas through a face mask. Prior art inhalation devices comprise indicator means that are visible to a party dispensing drugs to a patient, but which provide insufficient visual or sensory stimulus to directly induce the pediatric patient to maximize his breathing. One such prior art device is disclosed in U.S. Pat. No. 4,832,015 to Nowacki et al.

SUMMARY OF THE INVENTION

The present invention is directed toward an apparatus for inducing a pediatric patient to inhale a fluid pharmacological agent through a face mask. The invention comprises a fluid conduit having a first end and second end. The first end is capable of being coupled to a source of fluid pharmacological agent and the second end is capable of being coupled to a face mask sized to fit a pediatric patient such that fluid pharmacological agent flowing through the conduit can enter the face mask. The conduit has sufficient diameter to allow fluid pharmacological agent to flow through the conduit at a sufficient flow rate to be inhaled by a pediatric patient.

The invention further comprises a visual patient stimulator coupled to the conduit such that the inspiratory or expiratory flow of a patient's breath through the conduit activates the stimulator thereby causing it to change color. The coupling of the visual stimulator may be by mounting on the conduit or by remote attachment to the conduit, such as by electrical or electronic coupling. The stimulator is positioned such that when it is activated, it can be seen by a pediatric patient breathing gas through a face mask connected to the second end of the conduit. The activation of the stimulator results in a visible color change. The positioning of the stimulator may be by mounting on the conduit or, in the case of a remotely coupled stimulator, by placing or holding the stimulator in the patient's field of vision.

DESCRIPTION OF THE PREFERRED EMBODIMENTS

Figure 1:
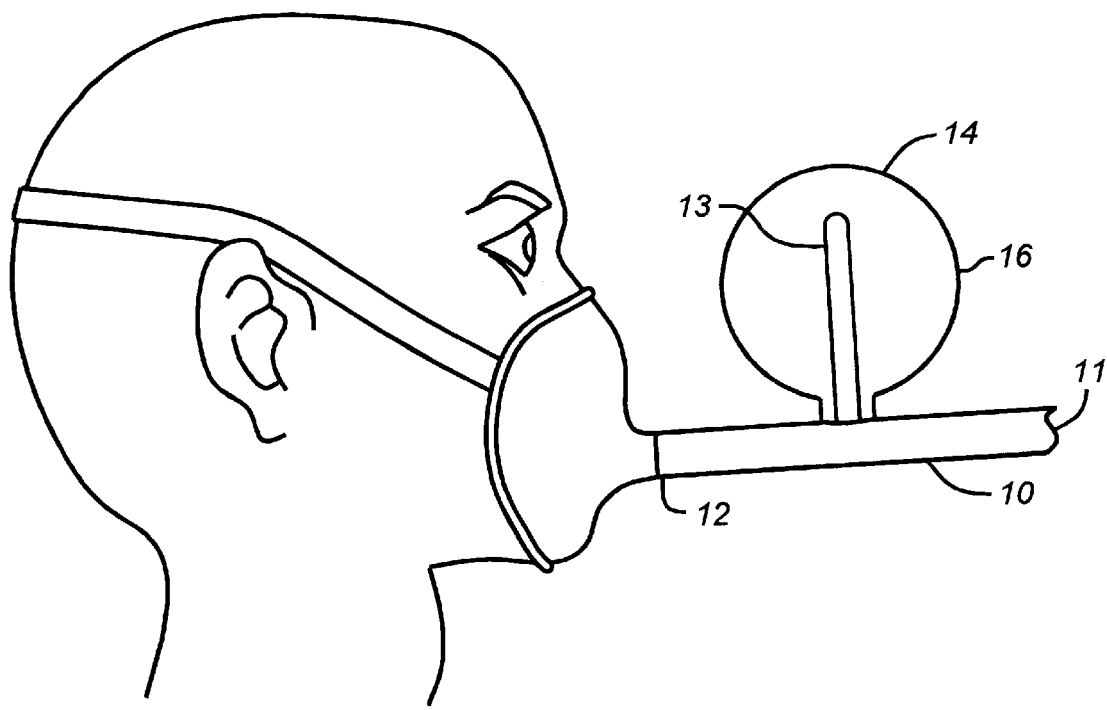
FIG. 1 is a side view of a first embodiment of the present invention being used by a pediatric patient.

As shown in FIG. 1, the invention comprises a fluid conduit 10 having a first end 11 and a second end 12. The first end is capable of being coupled to a source of fluid pharmacological agent. The second end is capable of being coupled to a face mask sized to fit a pediatric patient, such that fluid pharmacological agent flowing through the conduit can enter a face mask. The conduit has a sufficient diameter to allow fluid pharmacological agent to flow through it at a sufficient flow rate to be inhaled by a pediatric patent.

The invention further comprises a visual patient stimulator 14, coupled to the conduit such that inspiratory or expiratory flow of a patient's breath through the conduit activates the stimulator. The stimulator is positioned such that when it is activated, it provides a stimulus that is visible to a pediatric patient breathing gas through a face mask connected to the second end of the conduit.

In a preferred embodiment, the stimulator comprises a colorimetric member 13 that changes color in response to chemical colorimetric changes, as shown in FIG. 1. The inspiration and expiration of a pediatric patent through the fluid conduit cause changes in gas levels, such as carbon dioxide levels, which result in a visible color change in the stimulator. The colorimetric member may be an Easy Cap™ detection device, available from Nellcor Puritan Bennett of Pleasanton, Calif.

Figure 2:
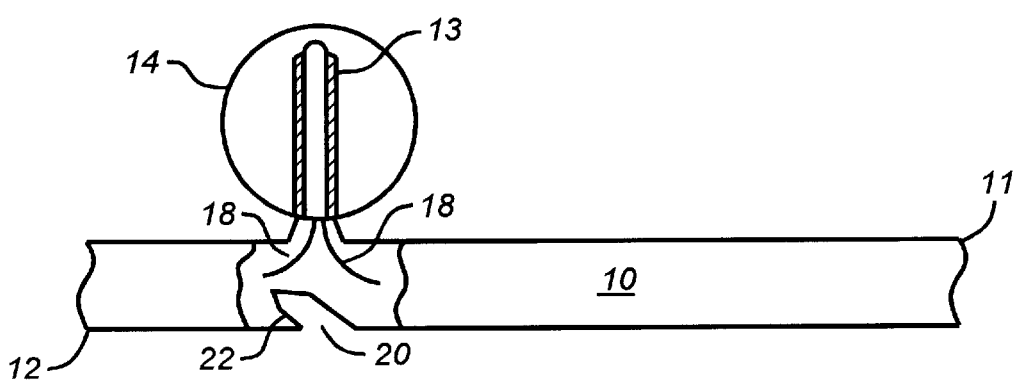
FIG. 2 is a cutaway side view of a second embodiment of the present invention.
Figure 3:
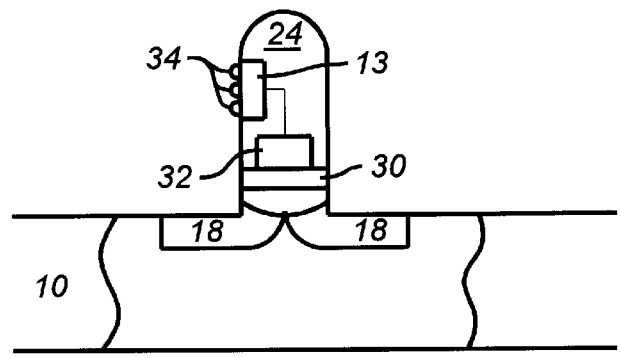
FIG. 3 is a side view of a third embodiment of the present invention.

In one preferred embodiment, as shown in FIG. 1, the colorimetric member is disc shaped, as shown in FIG. 3. In another preferred embodiment, the visual stimulator comprises a colorimetric carbon dioxide indicator. In a preferred embodiment, the invention further comprises a transparent housing 16 surrounding the colorimetric member, as shown in FIG. 2.

In another embodiment, as shown in FIG. 3, the visual stimulator comprises a carbon dioxide detector 30, a transducer 32, and a light indicator 34. The carbon dioxide detector is placed within the conduit. The transducer is coupled to the carbon dioxide detector such that when the carbon dioxide detector detects a predetermined level of carbon dioxide, the transducer sends an illumination signal to the light, resulting in the light being illuminated. Thus, the light indicator stays illuminated in response to the presence of a predetermined level of carbon dioxide in the conduit. In the embodiments shown in FIGS. 1, 3, and 4, any ports or openings on the surface of the conduit allow communication with a closed volume, such as a visual stimulator housing. In these embodiments conduit has no ports in communication with the ambient environment.

The illumination of the light indicator constitutes a visible color change that can be seen by a pediatric patient. The light source may comprise one or more individual lights of one or more colors as shown in FIG. 3.

Figure 4:
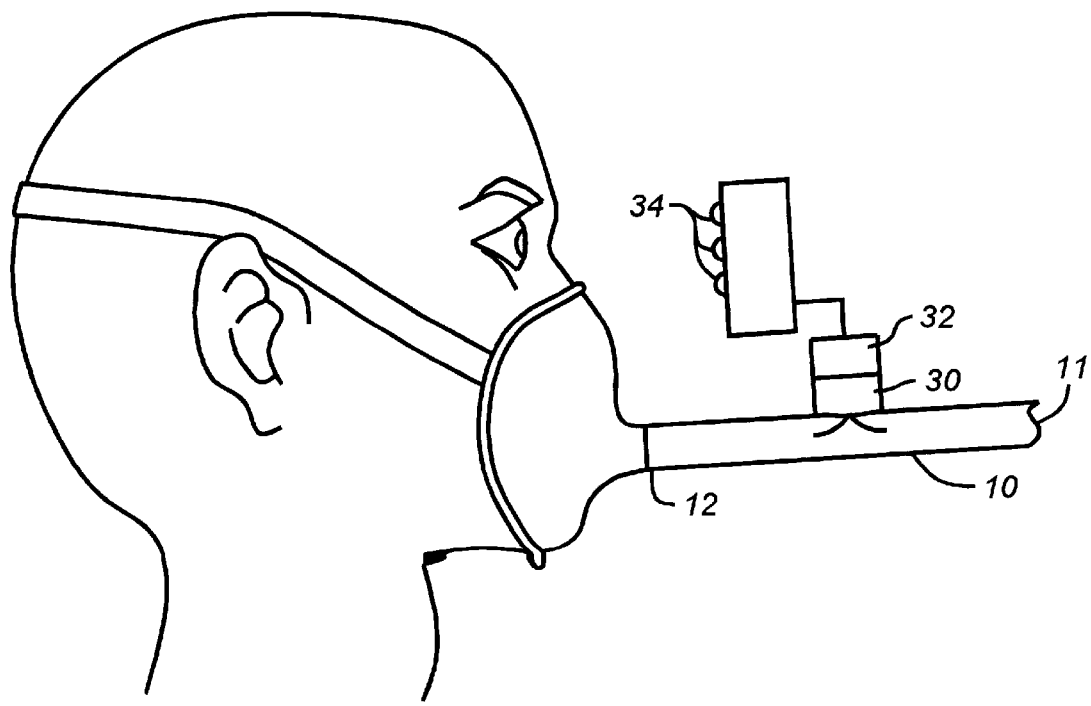
FIG. 4 is a side view of a fourth embodiment of the present invention.

In the embodiment of the invention shown in FIG. 4, the visual stimulator is a hand held unit coupled to the conduit. The coupling may be electrical, electronic, pneumatic or other means.

In a preferred embodiment, as shown in FIGS. 2 and 3, the invention comprises one or more baffles or flow deflectors 18 positioned in the conduit so as to deflect a portion of expiratory or inspiratory fluid flow in the conduct toward the colorimetric member.

In a preferred embodiment, the invention further comprises a fluid injection port 20 positioned in the fluid conduit, as shown in FIG. 2. In a preferred embodiment, the invention further comprises a flow diverter 22 positioned in the fluid conduit, such that fluid injected into the fluid injection port is directed toward the second end of the fluid conduit.

The foregoing disclosure and description of the invention are illustrative and explanatory thereof, and various changes in the size, shape and materials, as well as in the details of the illustrated construction, may be made without departing from the spirit of the invention.

What is claimed is:

1. An apparatus for inducing a pediatric patient to inhale a fluid pharmacological agent through a face mask, comprising:

a. a fluid conduit having a first end and a second end and no ports in communication with the ambient environment, said first end capable of being coupled to a source of fluid pharmacological agent and said second end capable of being coupled to a face mask sized to fit a pediatric patient such that fluid pharmacological agent flowing through said conduit can enter a face mask, said conduit having sufficient diameter to allow fluid pharmacological agent to flow through said conduit at a sufficient flow rate to be inhaled by a pediatric patient; and b. a visual patient stimulator coupled to said conduit such that the inspiratory or expiratory flow of a patients breath through said conduit causes said stimulator to change color, said stimulator being positioned such that its color change is visible to a pediatric patient breathing through a face mask connected to said second end of said conduit.

2. The apparatus of claim 1, wherein said visual stimulator comprises:

a. a colorimetric member that changes color in response to chemical colorimetric changes; and b. a transparent housing surrounding said colorimetric member.

3. The apparatus of claim 2, wherein said colorimetric member is disc shaped.

4. The apparatus of claim 2 further comprising at least one baffle positioned in said conduit so as to deflect a portion of inspiratory or expiratory fluid flow through said conduit toward said colorimetric member.

5. The apparatus of claim 1, wherein said visual stimulator comprises a colorimetric carbon dioxide indicator.

6. The apparatus of claim 1 wherein said visual stimulator comprises a light indicator which is illuminated in response to inspiratory or expiratory flow of a patient's breath sufficient to produce a predetermined level of carbon dioxide in said conduit.

7. An apparatus for inducing a pediatric patient to inhale a fluid pharmacological agent through a face mask, comprising:

a. a fluid conduit having a first end and a second end, said first end capable of being coupled to a source of fluid pharmacological agent and said second end capable of being coupled to a face mask sized to fit a pediatric patient such that fluid pharmacological agent flowing through said conduit can enter a face mask, said conduit having sufficient diameter to allow fluid pharmacological agent to flow through said conduit at a sufficient flow rate to be inhaled by a pediatric patient;

b. a visual patient stimulator coupled to said conduit such that the inspiratory or expiratory flow of a patients breath through said conduit causes said stimulator to change color, said stimulator being positioned such that its color change is visible to a pediatric patent breathing through a face mask connected to said second end of said conduit; and c. a fluid injection port positioned in said fluid conduit.

8. The apparatus of claim 7 further comprising at least one baffle positioned in said conduit so as to deflect a portion of inspiratory or expiratory fluid flow through said conduit toward said colorimetric member.

9. The apparatus of claim 7 further comprising a flow diverter positioned in said fluid conduit such that the fluid injected in said fluid injection port is directed towards said second end of said fluid conduit.

10. The apparatus of claim 7 wherein said visual stimulator comprises a colorimetric carbon dioxide indicator.

11. The apparatus of claim 7, wherein said visual stimulator comprises a light indicator which is illuminated in response to inspiratory or expiratory flow of a patient's breath sufficient to produce a predetermined level of carbon dioxide in said conduit.

12. The devise of claim 11 wherein said light indicator comprises at least two lights.

13. An apparatus for inducing a pediatric patient to inhale a fluid pharmacological agent through a face mask, comprising:

a. a fluid conduit having a first end and a second end, said first end capable of being coupled to a source of fluid pharmacological agent and said second end capable of being coupled to a face mask sized to fit a pediatric patient such that fluid pharmacological agent flowing through said conduit can enter a face mask, said conduit having sufficient diameter to allow fluid pharmacological agent to flow through said conduit at a sufficient flow rate to be inhaled by a pediatric patient;

b. a visual patient stimulator coupled to said conduit such that the inspiratory or expiratory flow of a patient's breath through said conduit causes said stimulator to change color, said stimulator being positioned such that its color change is visible to a pediatric patient breathing through a face mask connected to said second end of said conduit; and c. a baffle positioned in said conduit so as to deflect a portion of inspiratory or expiratory fluid flow through said conduit toward said visual stimulator.

14. The apparatus of claim 13, wherein said visual stimulator comprises:

a. a colorimetric member that changes color in response to chemical colorimetric changes; and b. a transparent housing surrounding said colorimetric member.

15. The apparatus of claim 14, wherein said colorimetric member is disc shaped.

16. The apparatus of claim 14 wherein said visual stimulator comprises a light indicator which is illuminated in response to inspiratory or expiratory flow of a patient's breath sufficient to produce a predetermined level of carbon dioxide in said conduit.

17. The apparatus of claim 14, wherein said visual stimulator comprises:

a. a carbon dioxide detector placed in said conduit.

b. a transducer coupled to said detector such that when said detector detects a predetermined level of carbon dioxide, each transducer emits an illumination signal; and c. a light indicator coupled to said transducer such that said light source is illuminated in response to an illumination signal from said transducer.

18. The apparatus of claim 17, wherein said carbon dioxide detector is a disc shaped colorimetric member.

* * * * *